United States Patent
Porter et al.

(10) Patent No.: US 6,887,077 B2
(45) Date of Patent: May 3, 2005

(54) IMMEDIATE LOAD DENTAL IMPLANT SYSTEM AND METHOD OF USE

(75) Inventors: Stephan S. Porter, Palm Beach Gardens, FL (US); Ralph E. Goodman, West Palm Beach, FL (US)

(73) Assignee: Implant Innovations, Inc., Palm Beach Gardens, FL (US)

(*) Notice: Subject to any disclaimer, the term of this patent is extended or adjusted under 35 U.S.C. 154(b) by 60 days.

(21) Appl. No.: 10/222,409

(22) Filed: Aug. 16, 2002

(65) Prior Publication Data

US 2003/0036036 A1 Feb. 20, 2003

Related U.S. Application Data

(60) Provisional application No. 60/313,301, filed on Aug. 17, 2001.

(51) Int. Cl.[7] .............................. A61C 8/00; A61C 3/02
(52) U.S. Cl. .......................... 433/174; 433/144; 606/79
(58) Field of Search .................................. 433/174, 172, 433/173, 175, 176, 201.1, 144; 606/79

(56) References Cited

U.S. PATENT DOCUMENTS

| | | | |
|---|---|---|---|
| 2,328,270 A | 8/1943 | Greenberg | 74/56 |
| 2,347,567 A | 4/1944 | Kresse | 32/12 |
| 2,588,006 A | 3/1952 | Hufnagel | 32/53 |
| 2,609,604 A | 9/1952 | Sprague | 433/174 |
| 2,721,387 A | 10/1955 | Ashuckian | 32/10 |
| 2,857,670 A | 10/1958 | Kiernan, Jr. | 32/10 |
| 3,576,074 A | 4/1971 | Gault et al. | 32/10 |
| 3,578,745 A | 5/1971 | Garnier et al. | 32/57 |
| 3,717,932 A | 2/1973 | Brainin | 32/10 A |
| 3,729,825 A | 5/1973 | Linkow et al. | 32/10 A |
| 3,747,216 A | 7/1973 | Bassi et al. | 32/57 |
| 3,827,145 A | 8/1974 | Richards | 32/10 A |
| 3,848,336 A | 11/1974 | Copeland | 32/59 |
| 3,921,044 A | 11/1975 | McShirley | 318/114 |
| 3,967,380 A | 7/1976 | Malata et al. | 32/27 |
| 3,969,823 A | 7/1976 | Nakanishi | 32/27 |
| 3,971,134 A | 7/1976 | Bokros | 32/10 A |
| 4,051,598 A | 10/1977 | Sneer | 32/10 A |
| 4,146,936 A | 4/1979 | Aoyagi et al. | 3/1.91 |
| 4,173,828 A | 11/1979 | Lustig et al. | 433/87 |
| 4,185,383 A | 1/1980 | Heimke et al. | 433/173 |
| 4,186,486 A | 2/1980 | Gordon | 433/201 |
| 4,199,864 A | 4/1980 | Ashman | 433/175 |
| 4,244,689 A | 1/1981 | Ashman | 433/175 |
| 4,252,525 A | 2/1981 | Child | 433/173 |
| 4,279,598 A | 7/1981 | Scheicher | 433/173 |

(Continued)

FOREIGN PATENT DOCUMENTS

WO   WO 95/21590   8/1995

OTHER PUBLICATIONS

Adell, R., et al., "A 15-Year Study of Osseointegrated Implants InOhe Treatment of The Edentulous Jaw," Int. J. Oral Surg., vol. 10, pp. 387–416 (1981).

(Continued)

*Primary Examiner*—John J Wilson
(74) *Attorney, Agent, or Firm*—Jenkens & Gilchrist (57) ABSTRACT

The present invention relates to a new dental implant that includes a generally cylindrical section and a tapered section. The implant has a thread making a plurality of turns around the exterior surface. The implant is installed into a bore that includes a generally cylindrical portion and a tapered portion. The dimensions of the cylindrical section and the tapered section of the implant are at least the dimensions of the generally cylindrical portion and the tapered portion of the bore, respectively. The bore is preferably shaped by a shaping drill that has a profile that generally mimics the profile of the implant. The female threads are preferably developed through a compression tap or a series of compression taps that cause the bone tissue defining the female threads to have increased density.

28 Claims, 4 Drawing Sheets

U.S. PATENT DOCUMENTS

| | | | |
|---|---|---|---|
| 4,289,849 A | 9/1981 | Lustig et al. | 433/123 |
| 4,290,756 A | 9/1981 | Sellers | 433/225 |
| 4,293,302 A | 10/1981 | Hassler et al. | 433/173 |
| 4,324,550 A | 4/1982 | Reuther et al. | 433/174 |
| 4,332,558 A | 6/1982 | Lustig | 433/86 |
| 4,392,827 A | 7/1983 | Martin | 433/32 |
| 4,411,624 A | 10/1983 | Ogino et al. | 433/173 |
| 4,463,753 A | 8/1984 | Gustilo | 128/92 B |
| 4,468,200 A | 8/1984 | Münch | 433/174 |
| 4,474,556 A | 10/1984 | Ellis et al. | 433/173 |
| 4,480,997 A | 11/1984 | Deutsch et al. | 433/221 |
| 4,492,577 A | 1/1985 | Farris et al. | 433/201 |
| 4,536,158 A | 8/1985 | Bruins et al. | 433/201.1 |
| 4,547,327 A | 10/1985 | Bruins et al. | 264/16 |
| 4,713,003 A | 12/1987 | Symington et al. | 433/173 |
| 4,713,006 A | 12/1987 | Hakamatsuka et al. | 433/201.1 |
| 4,722,688 A | 2/1988 | Lonca | 433/173 |
| 4,758,160 A | 7/1988 | Ismail | 433/173 |
| 4,773,858 A | 9/1988 | Marquez | 433/173 |
| 4,824,370 A | 4/1989 | Laurichesse et al. | 433/102 |
| 4,870,080 A | 9/1989 | Lamanec et al. | 514/289 |
| 4,886,456 A | 12/1989 | Ross | 433/173 |
| 4,992,045 A | 2/1991 | Beisel | 433/32 |
| 5,000,686 A | 3/1991 | Lazzara et al. | 433/174 |
| 5,004,422 A | 4/1991 | Propper | 433/175 |
| 5,026,387 A | 6/1991 | Thomas | 606/169 |
| 5,051,092 A | 9/1991 | Miller | 433/225 |
| 5,061,181 A | 10/1991 | Niznick | 433/174 |
| 5,199,873 A | 4/1993 | Schulte et al. | 433/174 |
| 5,205,745 A | 4/1993 | Kamiya et al. | 433/173 |
| 5,242,302 A | 9/1993 | Riehm | 433/164 |
| 5,259,398 A * | 11/1993 | Vrespa | 128/898 |
| 5,261,818 A | 11/1993 | Shaw | 433/165 |
| 5,312,255 A | 5/1994 | Bauer | 433/174 |
| 5,314,333 A | 5/1994 | Irmer et al. | 433/120 |
| 5,324,297 A | 6/1994 | Hood et al. | 606/99 |
| 5,324,299 A | 6/1994 | Davison et al. | 606/167 |
| 5,427,526 A | 6/1995 | Fernandes | 433/173 |
| 5,427,527 A | 6/1995 | Niznick et al. | 433/174 |
| 5,439,381 A | 8/1995 | Cohen | 433/173 |
| 5,443,468 A | 8/1995 | Johnson | 606/80 |
| 5,470,230 A | 11/1995 | Daftary et al. | 433/174 |
| 5,569,035 A | 10/1996 | Balfour et al. | 433/165 |
| 5,573,537 A | 11/1996 | Rogozinski | 606/80 |
| 5,575,650 A | 11/1996 | Niznick et al. | 433/165 |
| 5,591,029 A | 1/1997 | Zuest | 433/173 |
| 5,599,185 A | 2/1997 | Greenberg | 433/173 |
| 5,643,269 A | 7/1997 | Härle | 606/79 |
| 5,676,545 A | 10/1997 | Jones | 433/165 |
| 5,702,346 A | 12/1997 | Lazzara et al. | 433/173 |
| 5,709,547 A | 1/1998 | Lazzara et al. | 433/174 |
| 5,713,736 A | 2/1998 | Heath et al. | 433/102 |
| 5,718,707 A | 2/1998 | Mikhail | 606/94 |
| 5,727,943 A | 3/1998 | Beaty et al. | 433/174 |
| RE35,784 E | 5/1998 | Linkow et al. | 433/174 |
| 5,795,160 A | 8/1998 | Hahn et al. | 433/174 |
| 5,839,897 A | 11/1998 | Bordes | 433/165 |
| 5,842,865 A | 12/1998 | Bassett et al. | 433/174 |
| 5,863,201 A | 1/1999 | Lazzara et al. | 433/201.1 |
| 5,897,319 A | 4/1999 | Wagner et al. | 433/174 |
| 5,902,109 A | 5/1999 | Reams, III et al. | 433/174 |
| 5,997,298 A | 12/1999 | Nowak | 433/165 |
| 6,007,337 A | 12/1999 | Bauer | 433/173 |
| 6,099,313 A | 8/2000 | Dörken et al. | 433/175 |
| 6,106,292 A | 8/2000 | Hollander et al. | 433/165 |
| 6,132,214 A | 10/2000 | Suhonen et al. | 433/201.1 |
| 6,146,138 A * | 11/2000 | Dalmau | 433/141 |
| 6,171,312 B1 | 1/2001 | Beaty | 606/80 |
| 6,179,616 B1 | 1/2001 | Danger | 433/165 |
| 6,227,860 B1 | 5/2001 | Hobo | 433/173 |

OTHER PUBLICATIONS

Albrektsson, T., et al., "Osseointegrated Titanium Implants," Acta Orthop. Scand., vol. 52, pp. 155–170 (1981).

Implant Innovations, Inc., "Surgical Manual," 66 pages (Nov. 1996).

Implant Innovations, Inc., "TG Osseotite™ Single Stage Implant Surgical Manual," 8 pages (1998).

Innova Corp., "The Endopore™ Implant System," 8 pages, no date.

Instrument Makar, Inc., "Issues in ACL Reconstruction," 1 page, no date.

Nobelpharma, "Braånemark System™ Self–Tapping Fixtures," 8 pages (1989).

Nobelpharma, "Components For Installation Of Self–Tapping Fixtures," 4 pages (1989).

Richards Manufacturing Company, Inc., "Bone Screw Technical Information," 15 pages (1980).

Sargon Enterprises, Inc., "Sargon Immediate Load Implant," 6 pages, no date.

Straumann, "The ITI® Straumann SLA Surface," 4 pages (May 1988).

Summers, Robert B., DMD, "A New Concept In Maxillary Implant Surgery: The Osteotome Technique," Compend Contin Educ Dent, vol. XV, No. 2, pp. 152–160 (1994).

Summers, Robert B., DMD, "The Osteotome Technique: Part 2—The Ridge Expansion Osteotomy (REO) Procedure," Compend Contin Educ Dent, vol. XV, No. 4, pp. 422–434 (1994).

Summers, Robert B., DMD, "The Osteotome Technique: Part 3—Less Invasive Methods Of Elevating The Sinus Floor," Compend Contin Educ Dent, vol. XV, No. 6, pp. 698–708 (1994).

\* cited by examiner

IMMEDIATE LOAD DENTAL IMPLANT SYSTEM AND METHOD OF USE

RELATED APPLICATION

This application claims the benefit of priority of U.S. Provisional Patent Application No. 60/313,301, filed Aug. 17, 2001.

FIELD OF THE INVENTION

This invention relates generally to dental implants and, in particular, to a dental implant that can be immediately loaded by a prosthetic abutment, and to the tools and method that are used to prepare a bore for the implant.

BACKGROUND OF THE INVENTION

It is becoming more common to replace a missing tooth with a prosthetic tooth that is placed upon and attached to a dental implant. The dental implant serves as the artificial root that integrates with the bone tissue of the mouth. The prosthetic tooth preferably has a size and color that mimics the missing natural tooth. Consequently, the patient has an aesthetically pleasing and structurally sound artificial tooth.

One current surgical protocol by which implants are integrated into the patient involves two stages. In the first stage, the implant is inserted into the jawbone, covered by suturing the overlying gingival tissue, and allowed to osseointegrate for a period of three to six months. Covering the implant with the overlying gingiva minimizes the likelihood of infection around the implant and is believed to guard against disturbances that may slow its rate of osseointegration. The implants used in the two stage protocol are sometimes referred to as "subgingival implants."

After osseointegration is complete, the second stage is encountered in which the gingiva is again cut open and a gingival healing abutment is placed onto the implant. The overlying gingiva is sutured to allow it to properly heal around the healing abutment. When the healing abutment is removed and the prosthetic tooth is placed on the implant, the gingiva nicely conforms around the prosthetic tooth. It typically takes four to eight weeks, however, before the gingiva is healed. Thus, the overall procedure may take six to ten months.

Another implant surgical protocol requires one stage and uses an implant called a "transgingival implant" or "single-stage implant" that simultaneously promotes osseointegration and healing of the gingiva. This is accomplished by providing an implant that has a portion that integrates with the jawbone and a portion that extends through the overlying gingiva so that the gingiva properly heals therearound. Thus, the four to eight week gingival healing process in the two stage process occurs during the three to six month period of osseointegration. Consequently, the patient is fitted with a prosthesis in a shorter period of time. And, the gingiva is lacerated and sutured one less time compared with two stage systems which reduces the trauma to that region, the discomfort experienced by the patient, and minimizes the overall cost.

After the implant is installed in either the one stage or two stage surgical protocol, the implant is usually fitted with a low profile healing screw that covers the mechanical components (e.g., the threaded bore) at the gingival end of the implant that will later mate with the prosthesis. In other words, the implant does not typically receive a component that transfers forces or loads to the implant immediately after being installed. Of course, this means that the patient has a vacancy at the site where the implant has been installed until the prosthesis is attached to the implant.

To avoid this vacancy and achieve aesthetic results sooner, it has become more popular to provide a temporary prosthesis immediately after implant installation (i.e., "immediate loading"). It is desirable, however, to modify the existing implant designs and surgical protocols to further increase the success rate of implants that are immediately loaded.

SUMMARY OF THE INVENTION

The present invention relates to a new dental implant that includes a generally cylindrical section and a tapered section. The implant has a thread making a plurality of turns around the exterior surface. To support the implant in the bone, the male threads on the implant are relatively deep. For example, the major diameter of the thread is at least 25% larger than the minor diameter. The implant is installed into a bore that has been preferably constructed in a certain manner.

A bore in the bone includes a generally cylindrical portion and a tapered portion. The dimensions of the cylindrical section and the tapered section of the implant are at least the dimensions of, and possibly slightly larger than, the generally cylindrical portion and the tapered portion of the bore, respectively. The bore may further include a female thread in both the tapered portion and the generally cylindrical portion. The male threads of the implant mate with the female threads of the bore.

The bore is preferably shaped by a shaping drill that has a general profile that generally mimics the general profile of the implant. The female threads are preferably developed through a compression tap, or a series of compression taps, that causes the bone tissue defining the female threads to have increased density.

The above summary of the present invention is not intended to represent each embodiment, or every aspect, of the present invention. This is the purpose of the Figures and the detailed description which follow.

BRIEF DESCRIPTION OF THE DRAWINGS

The foregoing and other advantages of the invention will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE DRAWINGS

Figure 1A:
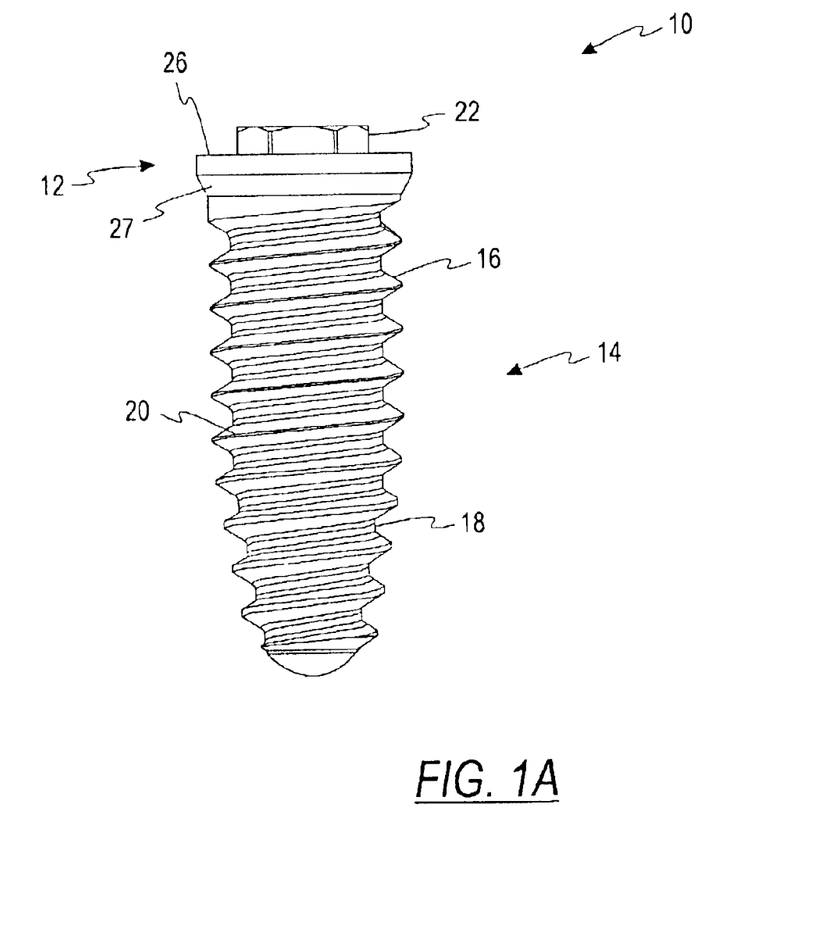
FIGS. 1A–1B are a side view and a top view, respectively, of an implant according to the present invention.
Figure 1B:
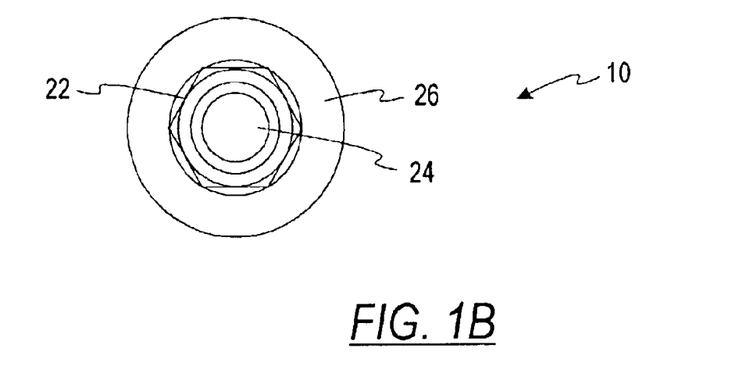

FIGS. 1A–1B illustrate an implant 10 capable of immediate loading, which includes an upper section 12 connected to a main body 14. The main body 14 includes a cylindrical section 16 and a tapered section 18. The exterior of the main body 14 includes a thread 20 that makes a plurality of turns through the cylindrical section 16 and the tapered section 18. The tapered section 18 tapers inwardly at an angle in the range of about 5° to about 15°.

The upper section 12 includes a hexagonal boss 22 that is useful for engaging the tool that applies torque to the implant 10 when the implant 10 is being installed. The hexagonal boss 22 is also used for non-rotationally engaging a correspondingly shaped socket on a prosthetic component (not shown) that is attached to the implant 10. The upper section 12 also includes the opening to a threaded bore 24 for receiving a screw that retains the prosthetic component on the implant 10. Such a component would have a surface for engaging a table 26, which is located around the hexagonal boss 22 on the upper section 12. The table 26 supports the prosthetic component mounted thereon. The upper section 12 preferably includes a chamfered surface 27 that connects the upper section 12 to the main body 14. The chamfered surface 27 supports the implant 10 in the bore.

In one preferred embodiment, the tapered section 18 tapers at an angle of 10° with respect to the central axis of the implant 10. This 10° taper applies to both the major and minor diameters of the thread 20. In this preferred embodiment, the thread 20 is relatively deep in that the minor diameter has a dimension of 3.5 mm (0.138 inch) and the major diameter has a dimension of 4.5 mm (0.177 inch). In other words, the difference between the major and minor diameters is 1.0 mm, whereas most similarly sized implants available in the market today have a difference of about 0.5 mm to about 0.7 mm. Stated slightly differently, the major diameter is at least 25% larger than the minor diameter. The lead of the thread 20 (i.e., the axial distance that the implant moves in one complete revolution) is 1 mm.

Figure 2A:
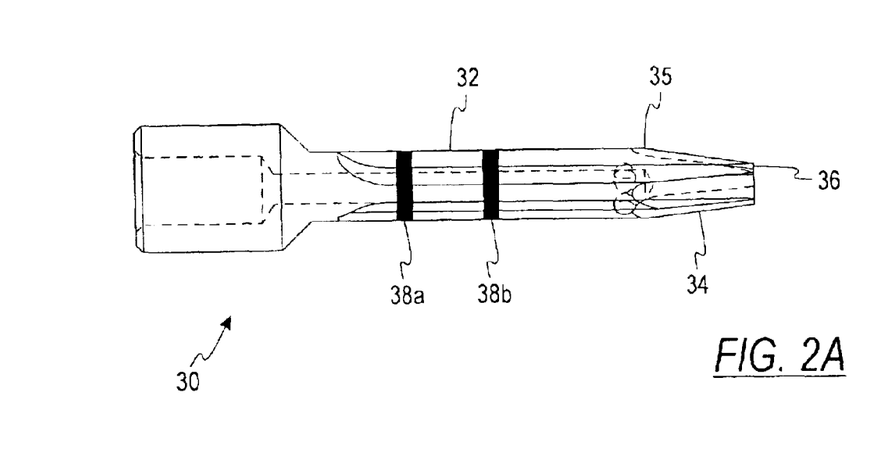
FIGS. 2A–2B are a side view and an end view, respectively, of a shaping drill according to the present invention.
Figure 2B:
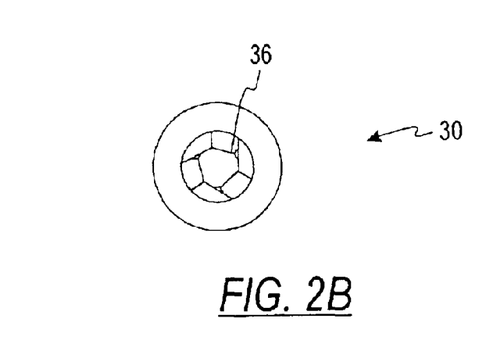

FIGS. 2A–2B illustrate a three flute shaping drill 30 that is useful for developing a bore in the bone having substantially the same profile as the implant 10. The shaping drill 30 includes a cylindrical portion 32 and a tapered portion 34. The cylindrical portion 32 and the tapered portion 34 meet at an intermediate point 35 along the length of the drill 30 that substantially corresponds to the point on the implant 10 where its tapered section 18 begins. The tapered portion 34 terminates at an end surface 36.

The drill 30 includes a plurality of depth markings 38 along its length. The depth markings 38 correspond to a known distance from the end surface 36. Each depth marking 38 is associated with a certain length of implant that is to be installed into the bone. For example, the lowermost depth marking 38a may be for an implant with a 10 mm length. The second depth marking 38b may be for an implant with a 13 mm length. Consequently, the same shaping drill 30 can be used to install several implants having the same diameter, but different lengths.

In the present embodiment, the cylindrical portion 32 of the drill 30 has an outer diameter that is substantially the same as the minor diameter of the thread 20 of the implant 10, and the tapered portion 34 of the drill 30 mimics the minor diameter of the tapered section 18 of the implant 10. This dimensional relationship may be more suitable for situations at sites where the bone is harder (i.e., the bone has a higher bone density).

Alternatively, when the bone is softer, the cylindrical portion 32 may preferably have a diameter that is slightly less than the minor diameter of the thread 20 of the implant 10. For example, the diameter of the cylindrical portion 32 of the shaping drill 30 may be 1 mm less than the minor diameter of the thread 20 of the implant 10. Thus, the major diameter of the thread 20 of the implant 10 may be 4.5 mm, the minor diameter may be 3.5 mm, and the outer diameter of the cylindrical portion 32 of the shaping drill 30 may be 2.5 mm. Furthermore, the tapered portion 34 of the drill 30 tapers at substantially the same angle as the tapered section 18 of the implant 10. Thus, the dimensions of the tapered portion 34 are slightly smaller than the corresponding dimensions on the minor diameter of thread 20 in the tapered section 18 of the implant 10. Consequently, when the implant is inserted into the bone, it will slightly compress the bone, increasing the localized bone density, and fit tightly within the bore that has been produced by the drill 30.

Figure 3:
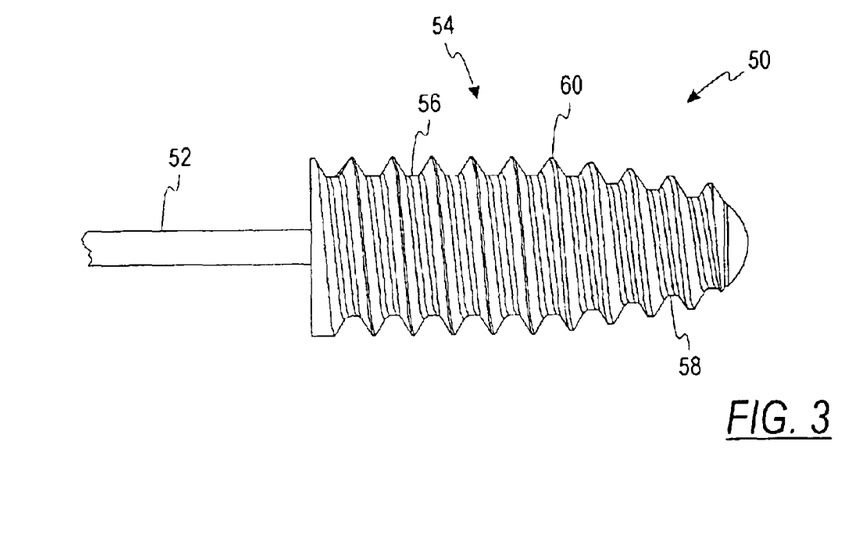
FIG. 3 is a side view of a compression tap of the present invention.
Figure 4A:
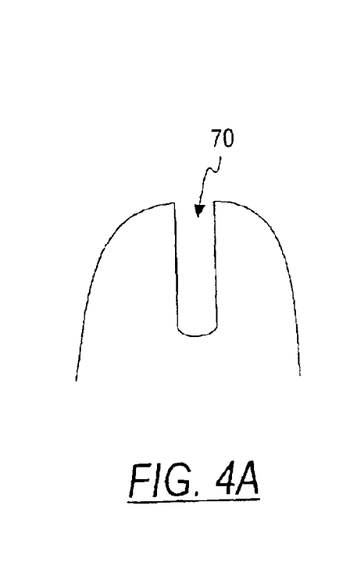
FIGS. 4A–4D are schematics of the bore being developed by the shaping drill and compression tap.
Figure 4B:
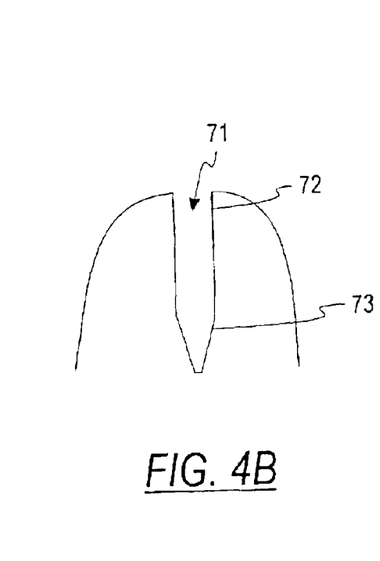
Figure 4C:
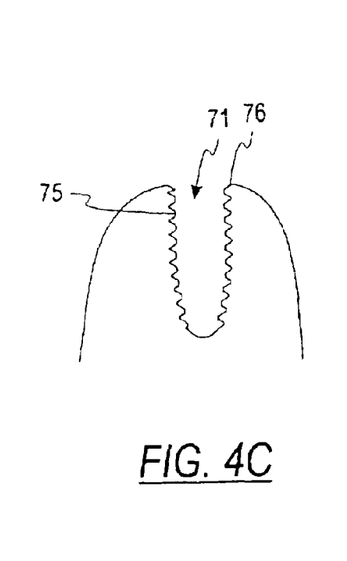
Figure 4D:
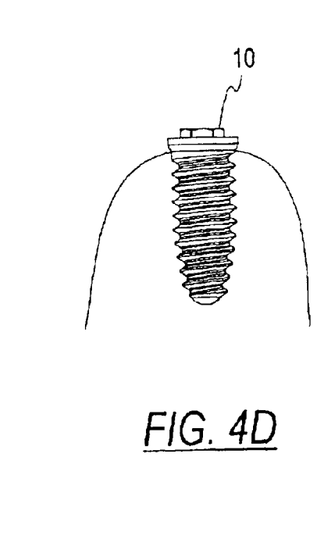

FIG. 3 illustrates a compression tap 50 that is used to develop a female thread in the bore in the bone. The tap 50 includes a shaft 52 and a main body 54. The main body 54 includes a cylindrical region 56 and a tapered region 58. A thread 60 extends through the cylindrical region 56 and the tapered region 58 on the body 54. The major diameter of the thread 60 is preferably smaller than the major diameter of the thread 20 of the implant 10. The minor diameter of the thread 60 in the cylindrical region 56 is the same diameter or slightly smaller than the diameter of the cylindrical portion 32 of the shaping drill 30. The lead of thread 60 is substantially the same as the thread 20 of the implant 10.

After the shaping drill 30 has been used to develop the general profile of the bore in the bone, the compression tap 50 is rotatably inserted into the bore to develop a female thread on the wall of the bone that defines the bore. Because the minor diameter of the thread 60 of the compression tap 50 is not as large as the diameter of the cylindrical portion 32 of the drill 30, the compression tap 50 only acts upon the wall of the bone along a helical locus within the bore that is defined by the thread 60.

The triangular cross-sectional shape of the thread 60 of the compression tap 50 is substantially the same as that of the thread 20 of the implant. Alternatively, the thread 60 may have a triangular cross-sectional shape that is slightly narrower at the root of thread 60 than the triangular cross-sectional shape of the thread 20 of the implant 10. Put slightly differently, the root width of the thread 60 of the compression tap 50 may be less than the root width of the thread 20 of the implant 10. Thus, rotatably inserting the implant 10 causes the thread 20 of the implant 10 to compress the bone further than the compression brought about by the compression tap 50. In yet a further possible alternative, the thread 20 of the implant 10 has a larger pitch diameter than the thread 60 of the compression tap 50.

Depending on the type of bone, a clinician may choose to use more than one shaping drill 30 and/or more than one compression tap 50 to prepare the bone for insertion of the implant 10. For example, the first compression tap may include a thread with a major diameter that is 0.5 mm less than the major diameter of the thread 20 of the implant 10. The next compression tap has a major diameter on its thread that may be 0.25 mm less than the major diameter of thread 20 of the implant 10. In other words, these series of compression taps 50 cause the female thread on the wall defining the bore to be gradually developed, causing less trauma to the area and a reduced chance for fracture of the cortical plates in the region. In addition to the gradual increase in the major diameter of the threads in the series of compression taps 50, the gradual increase can also be in the root width of the cross-section of the threads of the compression tap. Similarly, a series of shaping drills 30 can be used to gradually increase the dimensional characteristics of the bore. Also, because of the chamfered surface 27 of the implant 10, the bore may need to be shaped via a countersinking step to allow the chamfered surface 27 to rest on bone that has been appropriately angled.

It should be noted that where the bone tissue is quite soft, the implant 10 may be installed without the need for compression taps. In such cases, the rotation of the implant into the bore will result in the development of the female thread in the bore.

An important feature of the compression tap 50 relates to the fact that it is unlike a typical tap that scrapes the bone tissue in the bore to form the female thread and removes the scraped bone tissue from the bore. The compression tap 50 of the present invention creates the female thread in the wall defining the bore without removing much, if any, of the bone tissue from the bore. Thus, the female threads are defined by compressed bone tissue, which is denser than the original bone and thus stronger than the original bone. Consequently, when the implant 10 is installed into a bore that has been prepared by the shaping drill 30 and the compression tap 50 (or a series of compression taps), it is firmly secured in the bone and can transfer loads to the bone without damaging the implant site.

FIG. 4 summarizes one typical process by which the implant 10 of the present invention is installed in the bone. FIG. 4A illustrates a dental arch having a pilot hole 70 drilled therein. Once the pilot hole 70 has been formed, the shaping drill 30 is inserted into the pilot hole 70 to create a larger bore 71 having a cylindrical portion 72 and a tapered portion 73 as shown in FIG. 4B. The tapered portion 73 begins at a point prior to or at a bottom of the pilot hole 70. In some embodiments, the tapered portion 73 extends past the bottom of the pilot hole 70. In other embodiments, the tapered portion 73 ends at the bottom of the pilot hole 70. Next, the compression tap 50, or a series of compression taps, develops a female thread 75 in the bore 71 as shown in FIG. 4C. A countersink 76 may also be placed at the top of the bore 71 to engage the chamfered surface 27 of the implant. Finally, the implant 10 is installed into the prepared bore as shown in FIG. 4D.

In addition to creating denser bone tissue that engages and supports the implant 10, there are several features of the implant 10 that assist in resisting the movement of the implant 10 that could occur under typical loading, such as when the patient masticates. First, the tapering of the implant 10 at the tapered section 18 and the corresponding taper of the bore tend to keep the implant 10 from advancing further into the bore. Second, the increased depth of the thread 20 presents a larger surface area on the underside of the thread 20 that supports the implant 10 on the abutting bone tissue. Finally, the chamfered surface 27 also supports the implant 10 on the abutting bone tissue. Since the upper section 12 is placed at the crestal region of the bone where the harder cortical plates meet, the chamfered surface 27 is supported by bone tissue that is naturally denser than the cancellous bone located between the cortical plates.

In addition to or in lieu of the shaping drill 30, the clinician may form the osteotomy with compression-type osteotome tools. These tools are inserted into a pilot hole in the bore and advanced into the bore to force the bone tissue radially outward. The tools generally have a tapered shape that increases in cross-sectional area away from the distal end. Unlike drills, the osteotome compression tools remove little, if any, of the bone tissue from the bore. One set of osteotome tools is disclosed in U.S. Pat. No. 6,171,312, assigned to the assignee of the present application, which is incorporated herein by reference in its entirety. The '312 patent also discloses various drivers which can be used to impart motion (e.g., vibration) to the tools.

To enhance the integration of the implant 10 with the bone tissue, the tapered section 18 and a substantial portion of the cylindrical section 16 are preferably treated with the acid etching process that is disclosed in U.S. Pat. Nos. 5,876,453, 5,603,338 and 5,863,201, which are incorporated herein by reference in their entireties. The acid-etch treatment results in a microstructure having a roughened surface that includes a substantially uniform array of irregularities with peak-to-valley heights of less than 10 microns. Implants having this kind of surface are commercially available to the assignee of the present application under the trademark OSSEOTITE®.

Once the implant 10 has been properly installed in the bore, the clinician typically takes an impression of the site. Thus, an impression coping is attached to the upper section 12 of the implant and impression material is placed therearound. The impression is used to develop the final prosthesis that will be attached to the implant.

Figure 5:
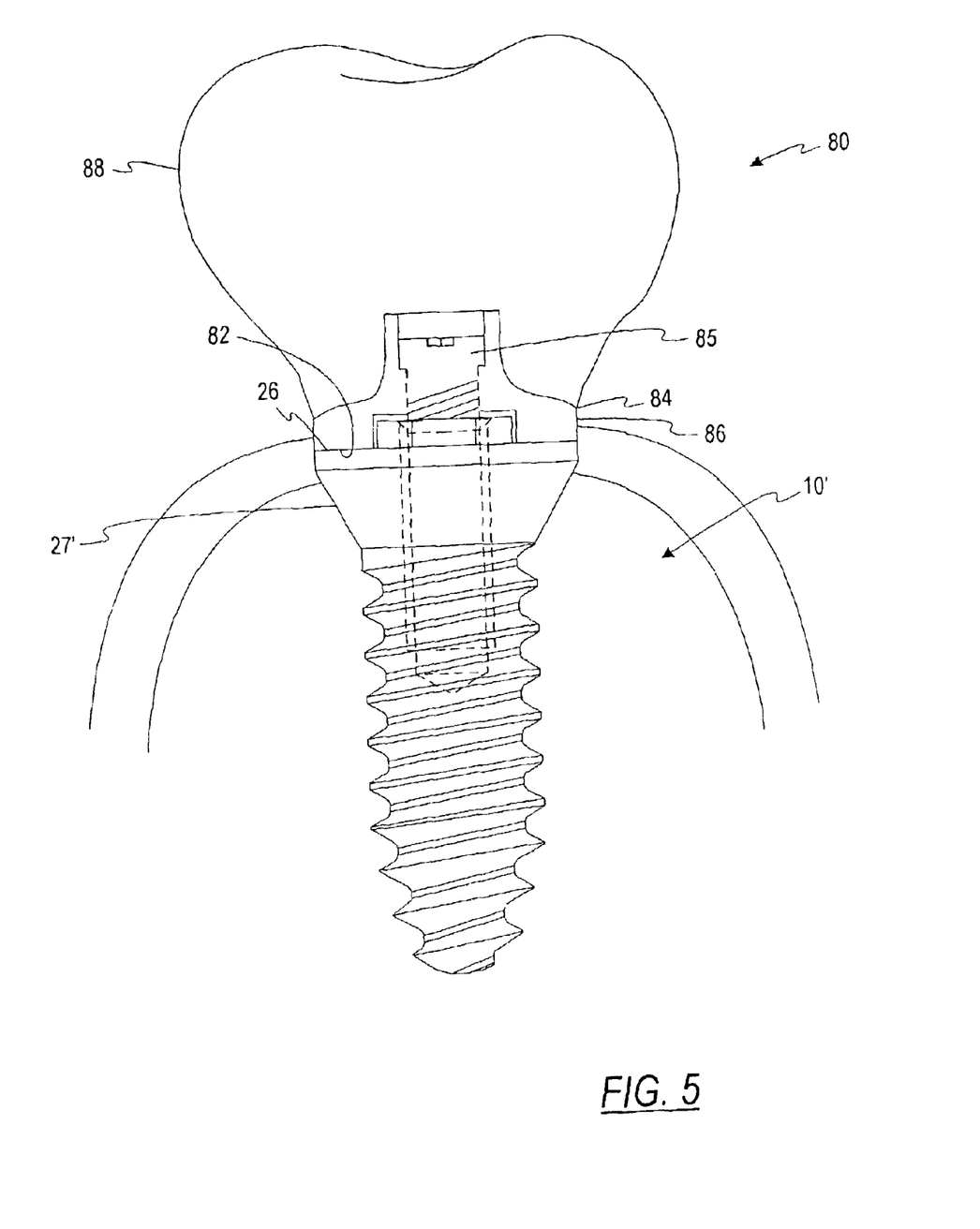
FIG. 5 is a side view of the temporary abutment attached to the dental implant for supporting a temporary prosthesis.

After the impression has been taken and the impression coping is removed, the clinician installs a temporary abutment on the implant 10. FIG. 5 illustrates one type of temporary abutment 80 that is attached to an implant 10'. The abutment 80 includes a lower surface 82 that engages the table 26 of the implant 10'. The abutment 80 includes a socket 84 that receives the hexagonal boss 22 for restricting the relative rotation of the two components. A screw 85 holds the abutment 80 on the implant 10'. The implant 10' is slightly different from the implant 10 in that this immediate load implant 10' has a larger chamfered surface 27' that is used for further supporting the implant 10' in the bone.

The abutment 80 also includes a smooth gingival collar 86 around which the gingiva can heal without irritation. The abutment 80 receives a dental material 88, such as acrylic, that can be modified by the clinician to fit within the adjacent teeth and have a height that does not present occlusal problems with the opposing teeth. In summary, the patient receives the dental implant 10 and an aesthetically pleasing prosthesis during the first visit to the clinician. Once the final prosthesis is complete, the patient again visits the clinician to have the final prosthesis replace the temporary prosthesis.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method for installing a dental implant that is capable of receiving an immediate load, comprising:

drilling a bore in bone, said bore having a length defined between a distal end located within said bone and a proximal end located at a surface of said bone;

enlarging said bore from said proximal end to an intermediate point along said length between said distal and proximal ends, said bore having a generally cylindrical portion between said proximal end and said intermediate point;

creating a tapered portion of said bore, said tapered portion beginning between said intermediate point and said distal end;

creating female threads in a bone wall defining said bore while removing an insubstantial amount of bone tissue from said bore, said female threads being located within said generally cylindrical portion and said tapered portion; and placing said dental implant into said bore, said implant having a generally cylindrical section with a diameter that is at least the diameter of said generally cylindrical portion of said bore and a tapered section with dimensions that are at least the dimensions of said tapered portion of said bore, said implant having male threads interfitting with said female threads of said bore.

2. The method of claim 1, wherein said step of creating said female threads includes the step of rotatably inserting a compression bane tap into said bore.

3. The method of claim 1, wherein said generally cylindrical section of said implant has a diameter that is greater than said generally cylindrical portion of said bore.

4. The method of claim 1, wherein said tapered section of said implant has dimensions that are greater than said tapered portion of said bore.

5. The method of claim 1, wherein said steps of enlarging said bore and creating said tapered portion of said bore include the step of rotatably inserting a drill bit having a tapered lower end.

6. The method of claim 1, wherein said male threads of said implant have a larger major diameter than said female threads in said bore.

7. The method of claim 1, wherein said intermediate point along said length is closer to said distal end of said bore than said proximal end.

8. The method of claim 1, wherein said step of creating female threads includes rotatably inserting in sequence at least two compression taps having progressively larger dimensions.

9. The method of claim 1, wherein said tapered portion of said bore and said tapered portion of said implant taper inwardly at an angle in the range of about 5° to about 15°.

10. The method of claim 1, wherein said steps of enlarging and creating occur simultaneously by use of a tapered shaping drill.

11. A kit of dental components for providing an immediate support for a prosthetic component, comprising:

a shaping drill for creating a bore having a cylindrical portion and a tapered portion;

a compression tap having a compression thread for creating a female thread in said bore without removing a substantial amount of bone tissue, said compression tap having a cylindrical upper portion and a tapered lower portion said compression thread being on said cylindrical upper portion and said tapered lower portion; and a dental implant for insertion into said bore and having an outer thread for insertion into said female thread of said bore, said dental implant having a cylindrical section and a tapered section that substantially correspond to said cylindrical upper portion and said tapered lower portion, respectively, of said compression tap.

12. The kit of claim 11, wherein said compression thread is substantially the same size as said outer thread.

13. The kit of claim 11, wherein said compression thread has a major diameter that is less than a major diameter of said outer thread.

14. The kit of claim 11, wherein said compression thread has a root thickness that is less than a root thickness of said outer thread.

15. The kit of claim 11, wherein said shaping drill, said compression tap, and said implant have lower ends that are tapered.

16. The kit of claim 11, wherein a major diameter on said outer threads on said implant is at least about 25% larger than a minor diameter on said implant.

17. A method for installing into bone a dental implant capable of receiving an immediate load, comprising:

creating a bore in said bone, said bore having a generally cylindrical proximal portion and a tapered distal portion;

compressing a bone wall defining said bore along a generally helical locus to produce female threads on said bone wall; and placing said dental implant into said bore, said implant having a generally cylindrical section with a diameter that is at least the diameter of said generally cylindrical portion of said bore and a tapered section with dimensions that are at least the dimensions of said tapered portion of said bore, said implant having male threads interfitting with said female threads of said bore.

18. The method of claim 17, wherein said step of creating said female threads includes the step of rotatably inserting a compression bone tap into said bore.

19. The method of claim 17, wherein said generally cylindrical section of said implant has a diameter that is greater than said generally cylindrical portion of said bore.

20. The method of claim 17, wherein said tapered section of said implant has dimensions that are greater than said tapered portion of said bore.

21. The method of claim 17, wherein said step of creating said bore includes the step of rotatably inserting a shaping drill having tapered lower end.

22. The method of claim 17, wherein said step of creating said bore includes the step of inserting a bone-compressing osteotome tool.

23. The method of claim 17, wherein said male threads of said implant have a larger pitch diameter than said female threads in said bore.

24. The method of claim 17, wherein said tapered portion is shorter than said cylindrical portion.

25. The method of claim 17, wherein said step of compressing a bone wall includes rotatably inserting at least two compression taps having progressively larger dimensions.

26. The method of claim 17, wherein said tapered portion of said bore and said tapered portion of said implant taper inwardly at an angle in the range of about 5° to about 15°.

27. A method for installing a dental implant capable of receiving an immediate load, comprising:

creating a bore in a bone that includes a tapered portion;

rotatably inserting a compression bone tap into said bore to create female threads in a bone wall defining said bore; and placing said dental implant into said bore, said implant having a generally cylindrical section and a tapered section, said cylindrical section and said tapered section having male threads tightly interfitting with said female threads of said bore.

28. The method of claim 27, wherein said tapered portion of said bore and said tapered portion of said implant taper inwardly at an angle in the range of about 5° to about 15°.

* * * * *

UNITED STATES PATENT AND TRADEMARK OFFICE
CERTIFICATE OF CORRECTION

PATENT NO. : 6,887,077 B2
DATED : May 3, 2005
INVENTOR(S) : Stephen S. Porter and Ralph E. Goodman It is certified that error appears in the above-identified patent and that said Letters Patent is hereby corrected as shown below:

<u>Column 7,</u>
Line 3, delete "bane" and insert -- bone --.

Signed and Sealed this

Fifteenth Day of November, 2005

JON W. DUDAS
*Director of the United States Patent and Trademark Office*